(12) United States Patent
Flohr et al.

(10) Patent No.: US 7,822,467 B2
(45) Date of Patent: Oct. 26, 2010

(54) METHOD FOR PRODUCING CT IMAGES OF A CYCLICALLY MOVING OBJECT TO BE EXAMINED

(75) Inventors: Thomas Flohr, Uehlfeld (DE); Bernd Ohnesorge, Erlangen (DE); Stefan Schaller, Fuerth (DE)

(73) Assignee: Siemens Aktiengesellschaft, Munich (DE)

( * ) Notice: Subject to any disclaimer, the term of this patent is extended or adjusted under 35 U.S.C. 154(b) by 363 days.

(21) Appl. No.: 10/984,834

(22) Filed: Nov. 10, 2004

(65) Prior Publication Data

US 2005/0101858 A1  May 12, 2005

(30) Foreign Application Priority Data

Nov. 10, 2003 (DE) ................. 103 52 380

(51) Int. Cl.
*A61B 5/05* (2006.01)
(52) U.S. Cl. ..................................... 600/428
(58) Field of Classification Search ............. 378/8, 378/15, 94, 4, 91, 110, 112, 113, 115, 95; 600/425, 428; 382/128, 131, 132
See application file for complete search history.

(56) References Cited

U.S. PATENT DOCUMENTS

| | | |
|---|---|---|
| 5,832,051 A | 11/1998 | Lutz |
| 6,266,553 B1 | 7/2001 | Fluhrer et al. |
| 6,466,640 B1 | 10/2002 | Taguchi |
| 6,504,893 B1 | 1/2003 | Flohr et al. |
| 6,556,697 B1 | 4/2003 | Bruder et al. |
| 2003/0007593 A1* | 1/2003 | Heuscher et al. ............... 378/4 |
| 2004/0114708 A1 | 6/2004 | Bruder et al. |

* cited by examiner

*Primary Examiner*—Brian Casler
*Assistant Examiner*—Elmer Chao
(74) *Attorney, Agent, or Firm*—Harness, Dickey & Pierce, P.L.C.

(57) ABSTRACT

A method is for producing CT images of at least one second organ cyclically excited to move by a first organ moving on its own, or examination area with rest phases and activity phases of a patient. The second organ or the examination area is scanned, preferably spirally. A three-dimensional image of the absorption coefficient is determined with the aid of a multiplicity of cutting planes on the basis of the data obtained by scanning in the rest phase of the second organ or examination area, and the movement information required to determine the rest phase is collected from the first organ.

18 Claims, 2 Drawing Sheets

METHOD FOR PRODUCING CT IMAGES OF A CYCLICALLY MOVING OBJECT TO BE EXAMINED

The present application hereby claims priority under 35 U.S.C. §119 on German patent application number DE 103 52 380.4 filed Nov. 10, 2003, the entire contents of which are hereby incorporated herein by reference.

FIELD OF THE INVENTION

The invention generally relates to a method for producing CT images of an organ, or examination area, cyclically excited to move, with rest phases and activity phases of a patient, through which the organ or the examination area is scanned, preferably spirally, and a three-dimensional image of the absorption coefficients is determined in the rest phase with the aid of a multiplicity of cutting planes on the basis of the data obtained by scanning.

BACKGROUND OF THE INVENTION

ECG-gated multi-row spiral investigations of the heart are generally known in the case of multi-row CT units. Reference may be made by way of example to DE 196 22 075 C2, DE 197 40 214 A1, DE 198 42 240 A1, DE 102 44 180 A1, DE 199 57 082 A1 or DE 198 42 238 A1. It is common to all these known methods for investigation of moving objects that during the investigation of the moving object the movement information or pulse energy is picked up from the moving object itself, which is to be displayed, the heart readily being selected in the concretely represented embodiments of the above-named patent applications as the organ to be scanned, and the signal information on the movement state being obtained by an ECG lead.

SUMMARY OF THE INVENTION

It is an object of an embodiment of the invention to find a way in which the objects to be examined that do not themselves initiate movement can be photographed with a reduced spatial unsharpness.

The inventors have found that even regions near the heart that are excited to move by the pulsation of the heart can be photographed with improved sharpness when only the data obtained during the rest phase of this pericardial environment are preferably used to reconstruct a CT image. However, with the known methods for producing CT images of a heart, it is only a very limited area corresponding to approximately 30% of the entire cardiac cycle that is used to produce images. According to an embodiment of the invention, however, it is possible to use a substantially larger area for imaging pericardial areas to be examined, since the transmission of movement of the heart to the neighboring regions occurs with much more damping than when the heart itself is considered.

A substantial advantage of an embodiment of this method resides in that a higher feed rate can be selected owing to the reduction of the cycle component that cannot be used, and so either a substantially larger area, for example the entire lung, can be swept in a breath-holding phase or, on the other hand, it is possible to operate using a substantially smaller section thickness of the individual tomograms.

According to this basic idea of an embodiment of the invention, the inventors propose a method for producing CT images of at least one second organ cyclically excited to move by a first organ moving on its own, or examination area with rest phases and activity phases of a patient, in which the second organ or the examination area being preferably spirally scanned by a gantry having at least one focus that radiates a conical beam onto to at least one opposite detector of multirow or planar design, the scanning, at a relative feed rate v in the z-direction between the gantry and patient, being performed in such a way that the scanned areas overlap or at least touch in the cyclically occurring rest phase, and a three-dimensional image of the absorption coefficients is determined with the aid of a multiplicity of cutting planes on the basis of the data obtained by scanning in the rest phase of the second organ or examination area, the movement information required to determine the rest phase being collected from the first organ.

It is preferred here for the heart to be used as first signaling organ, which initiates the movement, ECG signals preferably being used as movement information.

The lungs, the aorta area, the diaphragm, the liver, the spleen, the stomach and the intestines can be considered with reference to the imaged examination area or the second organ.

With reference to the relationship of the data used to reconstruct the CT images and discarded data of a movement cycle, the inventors propose that at least data from 50% of the cardiac cycle and at most 80% of the cardiac cycle, preferably data from 60-70% of the cardiac cycle are used for image reconstruction. This can be achieved, for example, by excluding from the reconstruction only the data determined by the R wave in the phase of strong movement.

It can be advantageous, furthermore, when the area in the cardiac cycle used for image reconstruction varies during a scan, preferably as a function of the distance from the heart. A smooth adaptation to the temporal extent of the movement of the section respectively considered can thereby be achieved. Again, a phase shift of the boundaries between a permitted and non-permitted area of the data used for reconstruction can be advantageous during a scanning pass on the basis of the time-delaying transmission path of the pulsation from the movement-initiating organ, for example the heart, to the currently scanned examination area. It is thus possible for the cycle area used for reconstruction to be adapted to the movement-initiating organ, for example the heart, with reference to its temporal extent or else to its phase, as a function of the area basically considered, or else of the area respectively just being scanned.

BRIEF DESCRIPTION OF THE DRAWINGS

The invention is explained in more detail below in an exemplary embodiment with the aid of the attached schematic drawings, the following reference numerals being used in the figures: 1 gantry, 2 x-ray tube with focus, 3 multirow detector, 4 patient couch, 5 z-axis, 6 control/evaluation unit with ECG, 7 patient, 8 ECG measuring lead, 9 control/data line to the gantry, 10 data use area, 11 ECG signal, 12 data segments used, v feed.

Of the figures, in detail.

DETAILED DESCRIPTION OF THE EXEMPLARY EMBODIMENTS

Figure 1:
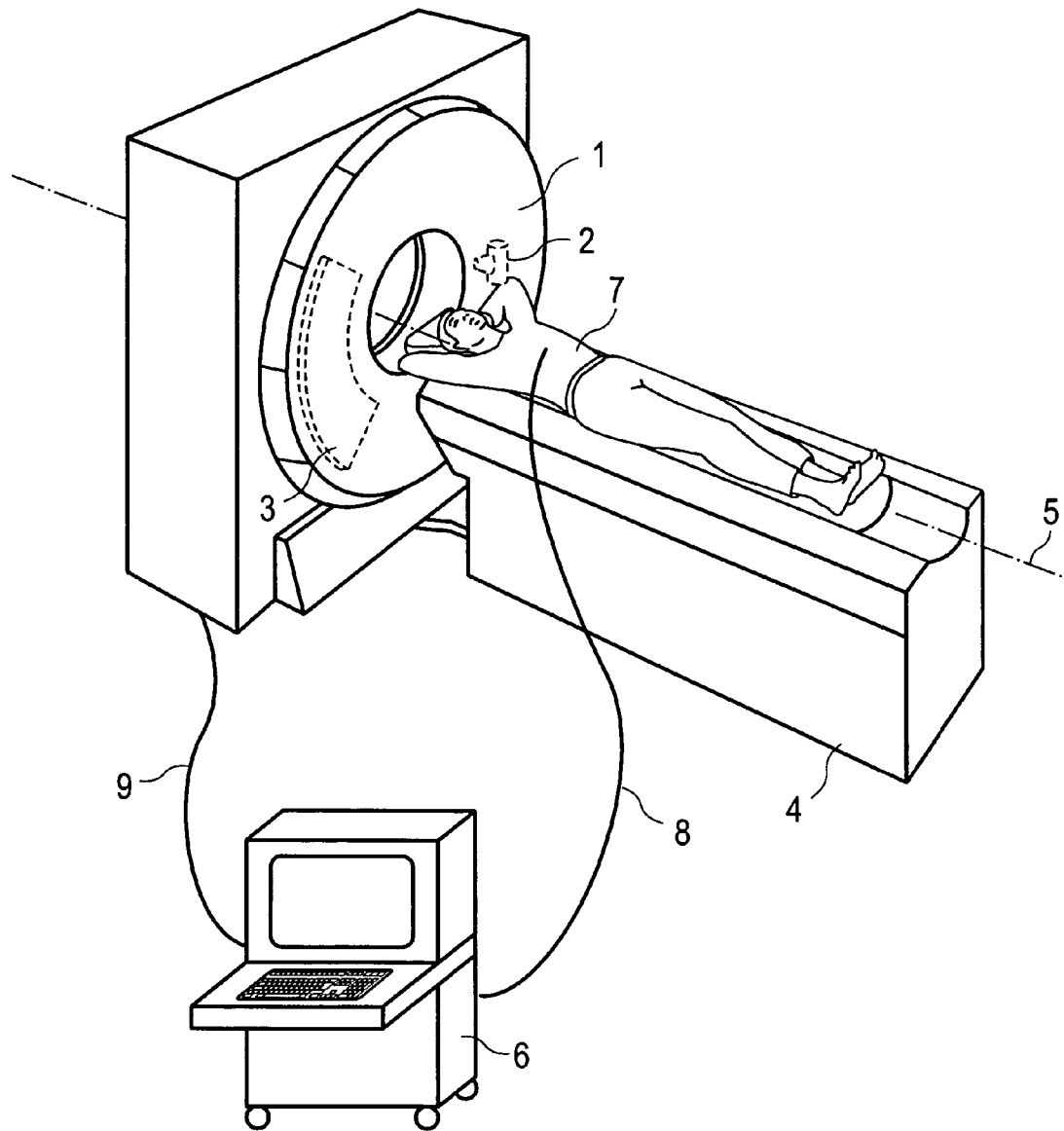
FIG. 1 shows a diagram of a CT.

FIG. 1 shows a diagram of a computed tomography unit having a gantry 1 and, integrated therein, an x-ray tube 2 with its focus and the multirow detector 3 situated opposite. Also shown is a patient couch 4 that can be displaced on the z-axis 5 and produces spiral scanning of the examination area by being fed in conjunction with the simultaneous rotation of the focus and the detector. A control/evaluation unit 6 is connected to the gantry 1 via a control/data line 9 such that the movement of the gantry 1, the control of the x-ray tube 2 and the simultaneous acquisition of data during scanning can take place. At the same time, ECG signals of the patient 7 are derived by means of an ECG, integrated in the evaluation unit 6, via the ECG measuring lead 8, and matched synchronously with the data streams from the detector. The measured data thereby receive "time stamps" from the detector that reproduce their phase relationship with the heart movement.

Figure 2:
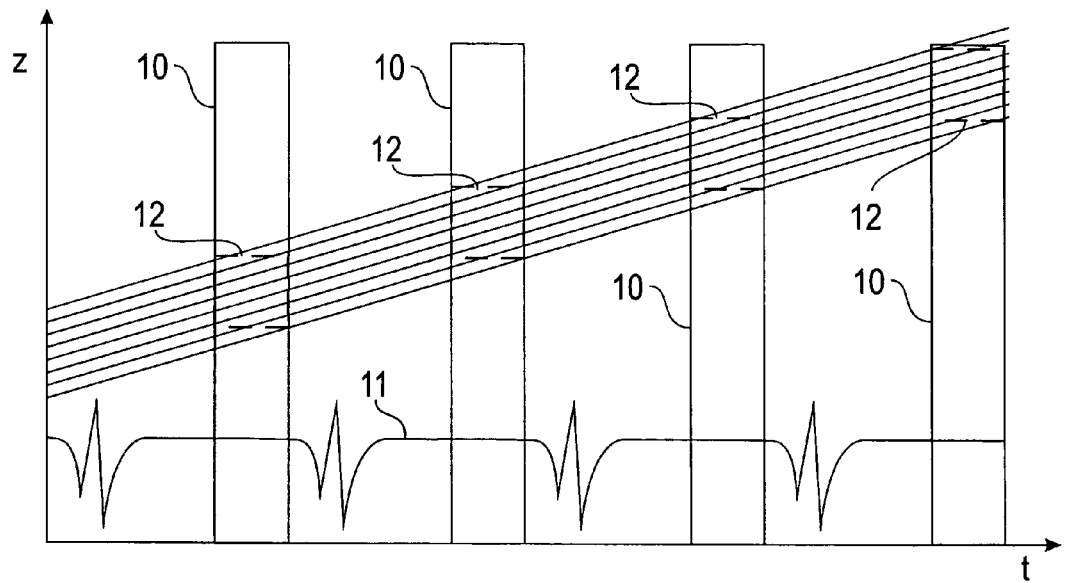
FIG. 2 shows a diagram of a known ECG-gated multirow spiral examination of the heart.

FIG. 2 shows a diagram of a known ECG-gated cardiac scan. In this illustration, the z-axis is represented against the time axis t, the profile of the ECG signal 11 being illustrated in relation to the feed in the lower coordinate area. The areas 10 define the rest phase of the heart, in which the actual data collection for reconstructing the CT images is performed, the areas 12 framed by dashes representing the so-called quick scan data segments of a scan, which are then used for data reconstruction.

During such a spiral reconstruction with optimized time resolution, such a quick scan data segment 12 is used for reconstruction for each image. Data segments 12 can be interpolated between the detector rows onto the respective image position within a quick scan.

As is known from the prior art, the quick scan data segment can in this case either be taken completely from one cardiac cycle, or be assembled from a number of partial segments from sequential cardiac cycles. It is characteristic of such a reconstruction that all data segments lie in a small relative phase of the cardiac cycle corresponding to a relative rest of the heart. This is indispensable for representing coronaries with few artifacts. The maximum couch feed that can be set then depends on the pulse rate, in order to ensure there are no gaps in the volume coverage.

When use is made of a four-row scanner with a rotation time of 0.5 sec, it is not possible to exceed a feed of 1.5 for low pulse rates (approximately 60 bpm). This suffices in order to cover the heart with 1 mm sections within a breath-holding phase, but is too little for lung examination or examinations of aortic dissections. If the pitch is raised with this mode of procedure, the result is a widening of the section sensitivity profile, as a result of which it is certainly possible to cover a larger volume within a breath-holding phase, but at the same time a worsened longitudinal resolution has to be accepted.

Figure 3:
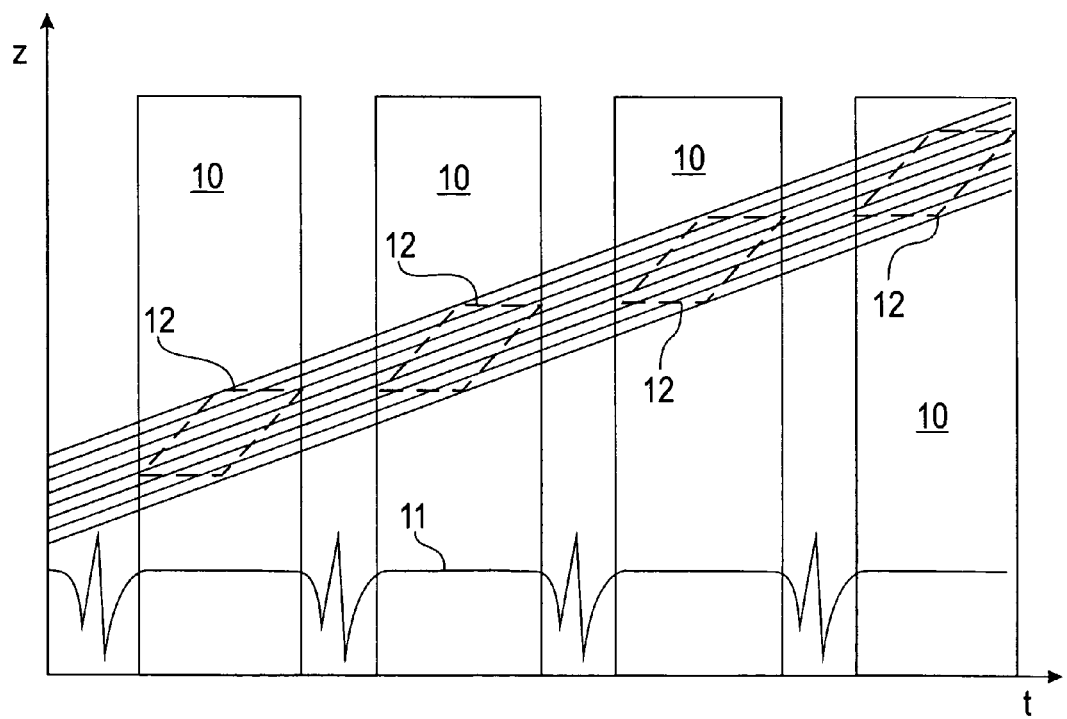
FIG. 3 shows a diagram of the method according to an embodiment of the invention, corresponding to FIG. 2.

FIG. 3 shows the same image as FIG. 2, but because it is not the moving organ itself, that is to say the heart, that is recorded, not only is a very narrow area 10 used here for data collection—but so, too, is a much wider area 10 in the cardiac cycle. A higher feed rate can be used correspondingly.

It is not necessary for all quick scan data segments 12 actually to be positioned in exactly the same relative phase of the respective cardiac cycle in order to suppress pulsation artifacts in these areas near the heart. Rather, it suffices to mark a specific area of the cardiac cycle as forbidden. This corresponds here to the phases of the cardiac cycle not covered by the area 10, which correspond here to the strongly moving systolic phase about the R wave.

In the remaining permitted data period 10, it is now possible to reconstruct each image from a quick scan interval, the result being a time resolution corresponding to half the rotation time. However, the quick scan interval 12 can float, that is to say the initial projections of the quick scan intervals are not permanently defined but shift with altered z-position of the image to be reconstructed within the permitted data area.

The respective quick scan segment 12 for an image is displaced in this way within the permitted data area such that it is optimally inserted into the spiral, and that spiral interpolation is possible between the detector rows onto the respective image position. The maximum feed of a four-row scan with a rotation of 0.5 sec can thereby be raised to approximately 3.5, a section thickness of 1 mm per image being achieved. This pitch of 3.5 then is sufficient to sweep more than 20 cm within the breath-holding phase.

Thus, overall an embodiment of the invention proposes a method for improved production of CT images of at least one second organ cyclically excited to move by a first organ moving on its own, or examination area with rest phases and activity phases of a patient, in which the second organ or the examination area is spirally scanned. A three-dimensional image of the absorption coefficients is determined with the aid of a multiplicity of cutting planes on the basis of the data obtained by scanning in the rest phase of the second organ or examination area, the movement information required to determine this rest phase being collected from the first organ.

As a result, on the one hand the spatial unsharpness of the observed second organ or examination area is greatly reduced by comparison with the recording without taking account of rest phases and activity phases, and correspondingly more detailed tomograms are achieved. On the other hand, the temporal restriction has a lesser effect than shown with photographs of the organ moving on its own where account is taken of the intensity of the transmission of the movement onto the observed organ that result in enlarged rest phases in which data can be collected. In addition, the magnitude and phase shift of the rest phase relative to the period of the organ moving on its own can also further be matched in accordance with the distance from the organ moving on its own. If appropriate, this can also take place smoothly during a scan.

It goes without saying that the features of the invention that have been mentioned above can be used not only in the combination respectively specified, but also in other combinations or on their own without departing from the scope of the invention.

What is claimed is:

1. A method for producing CT images of a patient with an autonomously cyclically moving heart with temporal areas of rest phases and activity phases and a region of interest, where the region of interest is located a distance away from the heart and has different temporal areas of rest phases and activity phases than the heart, the method comprising:

monitoring the cyclic moving of the heart and detecting the temporal areas of rest phases of the heart;

scanning the region of interest by a gantry including at least one x-ray tube with a focus that radiates a conical beam onto at least one opposite detector of at least one of multi-row and planar design;

scanning at a relative feed rate in the z-direction between the gantry and patient in such a way that the scanned areas during a cyclically occurring rest phase at least touch; and reconstructing CT images of the patient using data that is received from a scan in which at least the rest phases of the region of interest are calculated according to the distance between the scanned region of interest and the heart, with the monitored cyclic moving of the heart being used as a temporal reference.

2. The method as claimed in the claim 1, wherein the rest phases of the region of interest used for reconstruction are adapted with reference to the temporal areas of the rest phases to the heart as a function of the distance of the area fundamentally considered.

3. The method as claimed in claim 1, wherein the rest phases of the region of interest used for reconstruction are adapted with reference to a temporal areas of the rest phases to the heart as a function of the distance of the area respectively just scanned.

4. The method as claimed in claim 1, wherein, for reconstruction purposes, the rest phases of the region of interest used are adapted with reference to the rest phases relative to the heart as a function of the distance of the area fundamentally considered from the heart.

5. The method as claimed in claim 1, wherein, for reconstruction purposes, the rest phases of the region of interest used are adapted with reference to the rest phases relative to the heart as a function of the distance of the area respectively just scanned from the heart.

6. The method as claimed in claim 1, wherein the monitoring the cyclic moving includes using ECG signals.

7. The method as claimed in claim 1, wherein the region of interest are lungs.

8. The method as claimed in claim 1, wherein the region of interest is an aorta.

9. The method according to claim 1, wherein the region of interest is a diaphragm.

10. The method as claimed in claim 1, wherein the region of interest is a liver.

11. The method as claimed in claim 1, wherein the region of interest is a spleen.

12. The method as claimed in claim 1, wherein the region of interest is a stomach.

13. The method as claimed in claim 1, wherein the region of interest is intestines.

14. The method as claimed in claim 1, wherein data from a range of 50-80% of a cardiac cycle of the heart are used for image reconstruction.

15. The method as claimed in claim 1, wherein data from a range of 60-70% of a cardiac cycle of the heart are used for image reconstruction.

16. The method as claimed in claim 1, wherein the scanning the region of interest includes spiral scanning by the gantry.

17. The method as claimed in claim 1, wherein a magnitude and phase shift of the rest phases of the region of interest relative to the cyclic moving of the heart are matched in accordance with the distance of the region of interest from the heart.

18. An apparatus for producing CT images of a patient with an autonomously cyclically moving heart with temporal areas of rest phases and activity phases and a region of interest, where the region of interest is located a distance away from the heart and has different temporal areas of rest phases and activity phases than the heart, the apparatus comprising:
  means for monitoring the cyclic moving of the heart and detecting the temporal areas of rest phases of the heart;
  means for scanning the region of interest by a gantry including at least one x-ray tube with a focus that radiates a conical beam onto at least one opposite detector of at least one of multi-row and planar design;
  means for scanning at a relative feed rate in the z-direction between the gantry and patient in such a way that the scanned areas during a cyclically occurring rest phase at least touch; and
  means for reconstructing CT images of the patient using data that is received from a scan in which at least the rest phases of the region of interest are calculated according to the distance between the scanned region of interest and the heart, with the monitored cyclic moving of the heart being used as a temporal reference.

* * * * *